Figure 1:
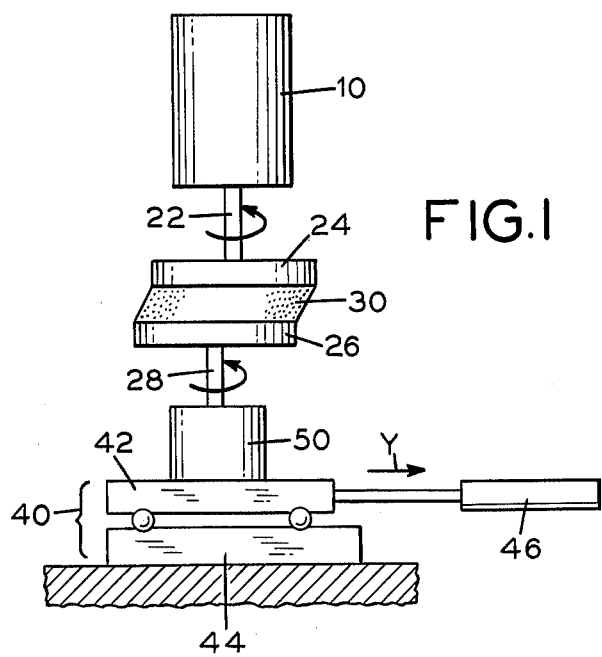

United States Patent [19]

Starita

[11] 4,095,461
[45] Jun. 20, 1978

[54] RHEOLOGICAL TEST METHOD AND APPARATUS

[76] Inventor: Joseph M. Starita, 13 Beverley Dr., Belle Mead, N.J. 08502

[21] Appl. No.: 754,753

[22] Filed: Dec. 27, 1976

[51] Int. Cl.² .................. G01N 3/24; G01N 25/02
[52] U.S. Cl. ...................... 73/101; 73/15.6; 73/91
[58] Field of Search ................. 73/89–91, 73/101, 103, 15.4, 15.6, 54, 58, 60

[56] References Cited

U.S. PATENT DOCUMENTS 3,535,914 10/1970 Veith et al. ............... 73/101 X
3,982,427 9/1976 Decker ...................... 73/101

OTHER PUBLICATIONS

Rheometrics, Inc.; "The Mechanical Spectrometer"; (11-1975).

*Primary Examiner*—Richard C. Queisser
*Assistant Examiner*—Charles Gorenstein
*Attorney, Agent, or Firm*—Davis, Hoxie, Faithfull & Hapgood

[57] ABSTRACT

Rheological property measurement employing eccentric rotating disc apparatus wherein measurements of viscous and elastic force data are made at multiple displacements of the disc axes to cancel errors.

4 Claims, 9 Drawing Figures

RHEOLOGICAL TEST METHOD AND APPARATUS

BACKGROUND

Rheology is the study of deformation and flow of matter. Understanding of the processing qualities of polymers including elastomers is enhanced by the ability to measure dynamic loss modulus V (G") related to viscosity and dynamic storage modulus E (G') related to elasticity. Polymers having similar dynamic loss moduli may process quite differently in the manufacture of products from the polymers. Polymers having similar dynamic loss moduli and similar dynamic storage moduli, that is similar viscosities and similar elasticities, will likely process similarly. Therefore, the ability to characterize polymers in terms of both viscous and elastic properties is valuable to those who process or supply polymers.

SUMMARY OF THE INVENTION

The present invention is concerned with rheological measurement of viscoelastic properties using eccentric rotating disc apparatus in a manner which eliminates errors due to mechanical or electrical misalignment or imbalance.

Figure 2:
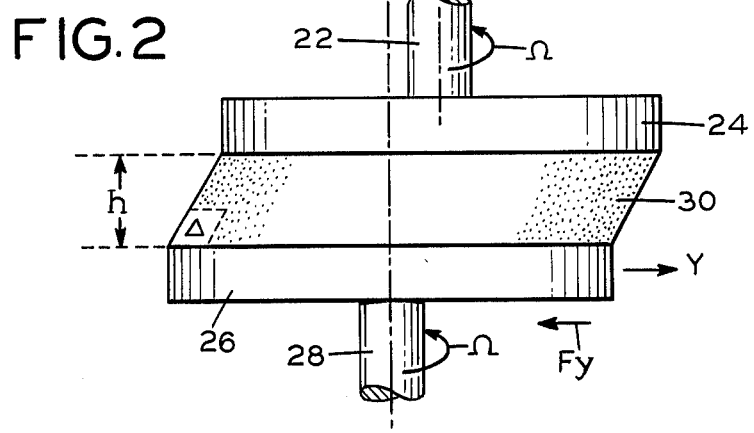
Figure 3:
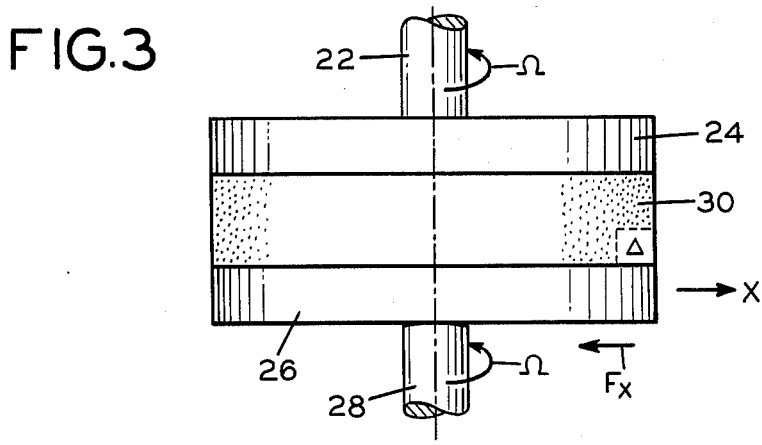
Figure 5:
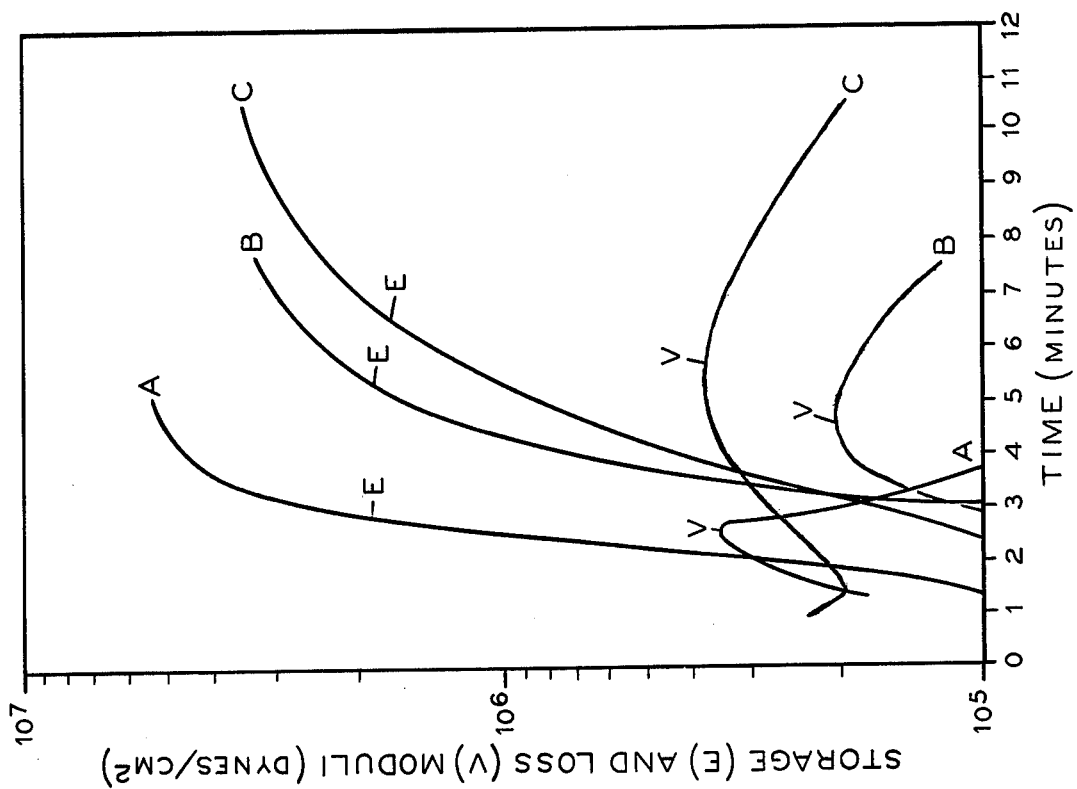
Figure 4:
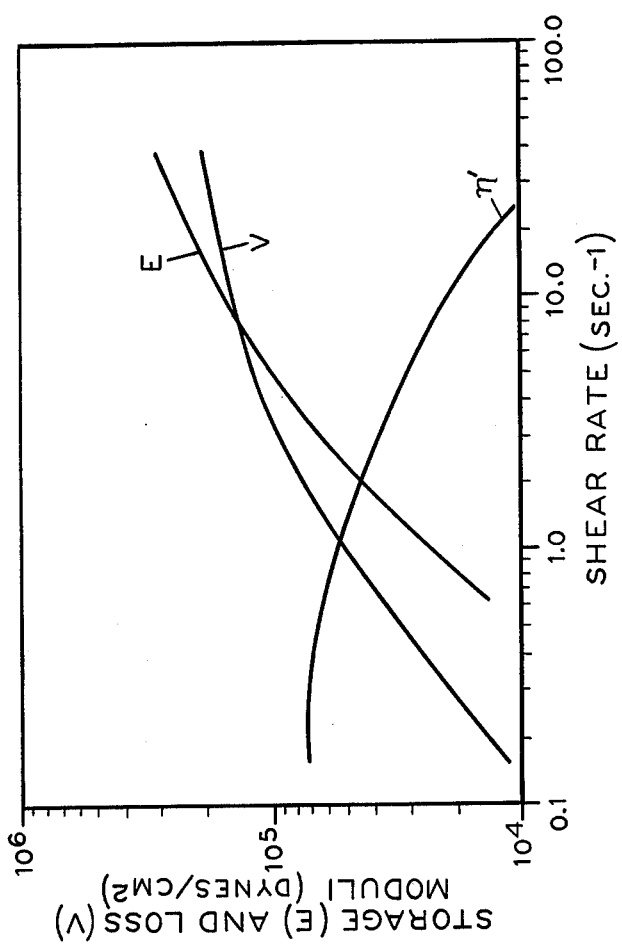
Figure 6:
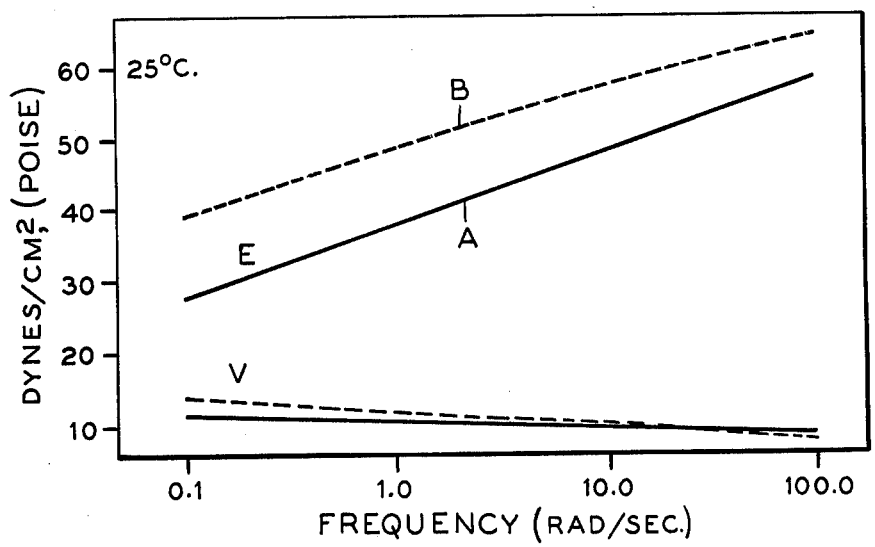
Figure 7:
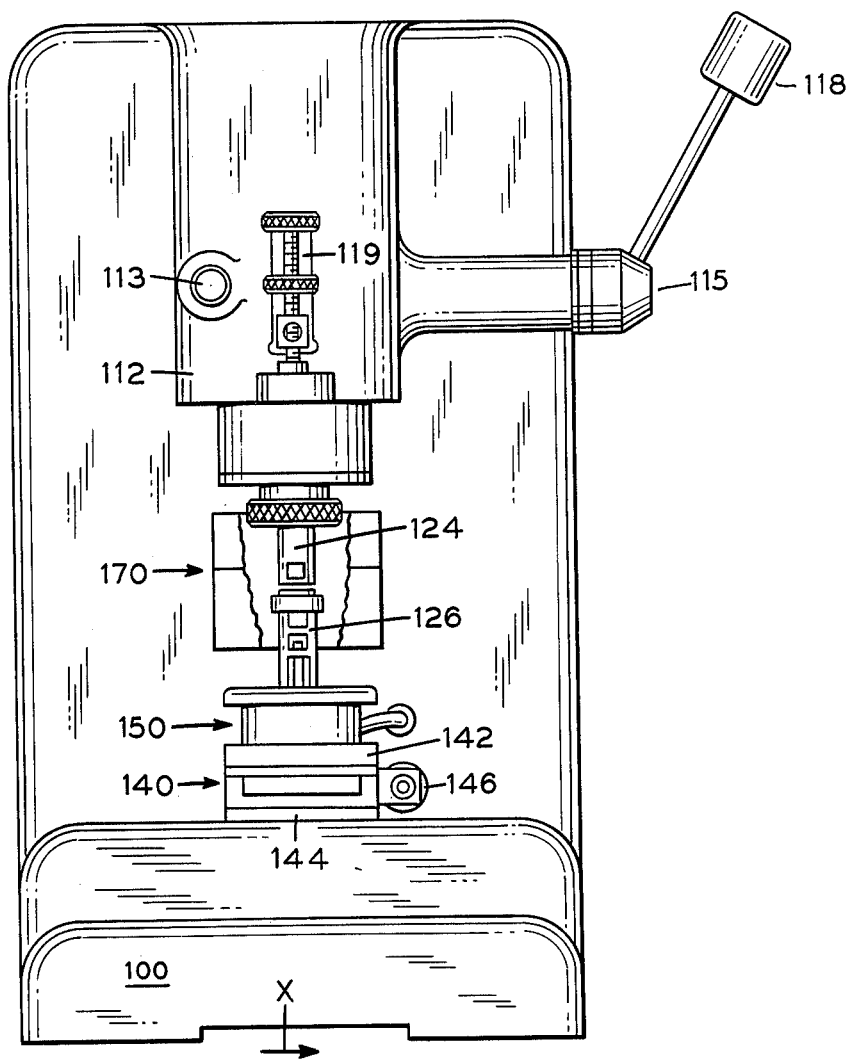
Figure 8:
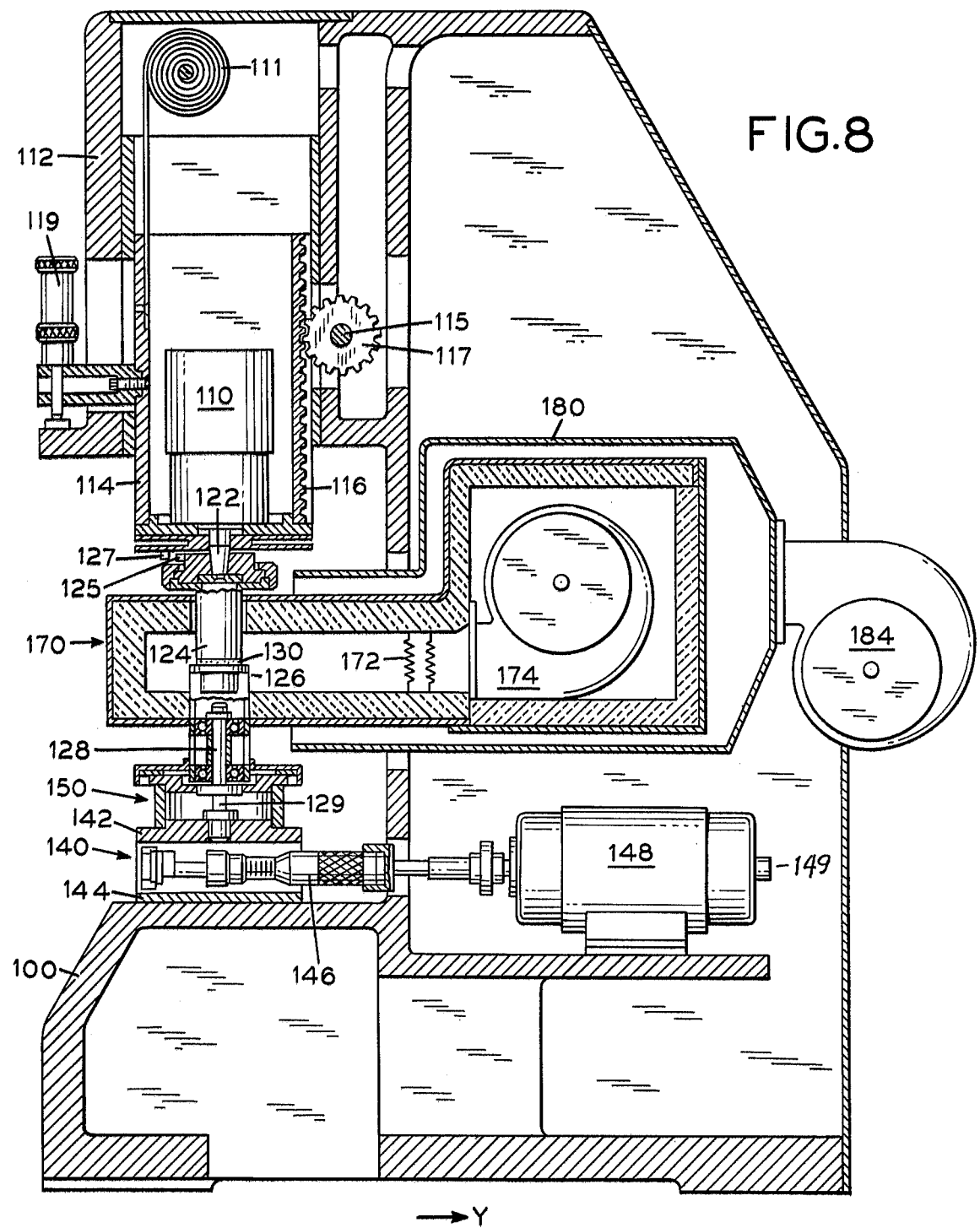
Figure 9:
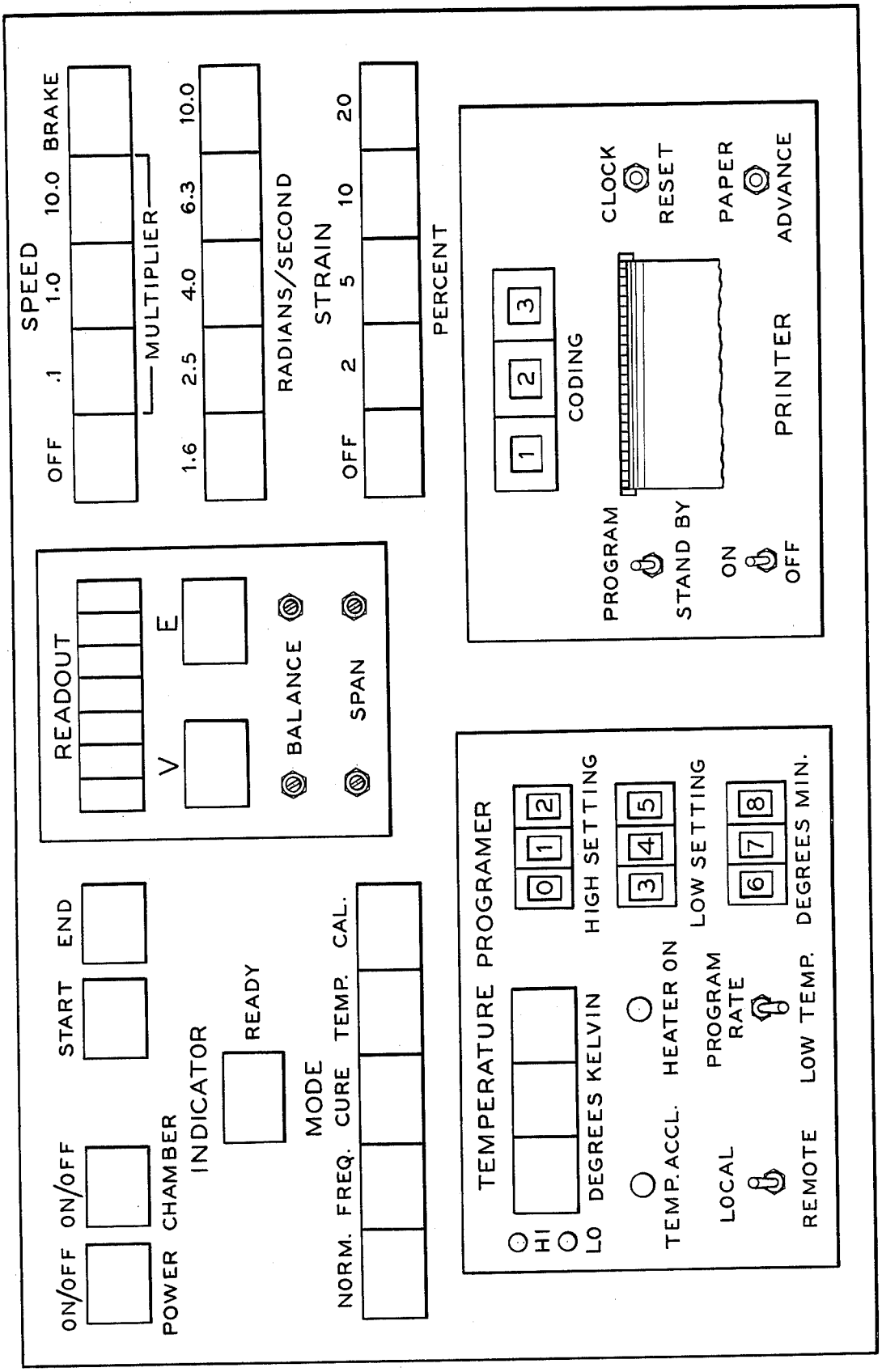

In the drawings:

FIG. 1 is a schematic view of apparatus for measuring viscoelastic properties,

FIG. 2 is a schematic view of the eccentric rotating discs of the apparatus of FIG. 1 as seen along the X axis, FIG. 3 is a schematic view similar to that of FIG. 2, but as seen along the Y axis, FIG. 4 is a plot of rheological properties of a polystyrene, FIG. 5 is a plot of rheological properties of three epoxy/glass molding compounds, FIG. 6 is a plot of rheological properties of two ethylene propylene diene elastomers, FIG. 7 is a front elevational view of apparatus in accordance with the present invention, FIG. 8 is a side elevational view in section of the apparatus of FIG. 7, and FIG. 9 is an elevational view of the control panel for the apparatus of FIG. 7.

A wide variety of techniques have been used to measure viscoelastic properties in polymers. One of the better techniques employs eccentric rotating disc or orthogonal rheometer apparatus as shown schematically in FIG. 1. A servo motor 10 having an output shaft 22 rotates the upper driving disc 24 at selected angular velocities. A sample 30 of polymer to be evaluated is interposed between the confronting parallel faces of a driving disc 24 and a lower driven disc 26 freely rotatably supported by a shaft 28. Shaft 28 is supported by a low friction bearing affixed to the upper platform 42 of a stage 40. The upper platform 42 is displaceable preselected distances in the Y axis direction with respect to the fixed lower platform 44 by a linear actuator 46. Forces on the shaft 28 are measured by a force transducer 50 having separate x direction and orthogonally positioned y direction electrical force transducers such as strain gages or piezo-resistive devices having electrical resistance signal characteristics proportional to the imposed strains.

According to the invention the dynamic storage or elastic modulus E and the dynamic loss or viscous modulus V are determined using this eccentric rotating disc geometry. The technique measures both dynamic moduli simply and directly. Referring to FIGS. 2 and 3, the two discs 24 and 26 rotate about parallel axes that have been laterally displaced a small predetermined amount $y$ in the Y axis direction. The sample, of thickness $h$, is confined between the confronting parallel faces of the discs and, due to the eccentricity, is forced to go through a shear cycle with each rotation. FIG. 2 is a view displaced 90° from FIG. 3. As the discs rotate 90°, elements of the sample are subjected to a shear deformation of a distance $y$ as shown in FIG. 2. As the discs continue to rotate another 90°, the displaced elements of the sample are returned. This displacement or shear strain results in a shear stress or force on the surface of each disc. $F_y$ is the elastic component of that force in the Y axis direction. $F_y$ tends to return to sample to its undeformed state. It is a measure of the energy stored and is related to the elastic modulus E by the factor of stress divided by strain:

$$E = (F_y/\pi R^2)/(y/h) = \text{Elastic Shear Modulus}$$

Real materials also dissipate energy when deformed. Thus, there normally will be a viscous component of the shear force. The viscous component appears as $F_x$; the shear force component in the direction of the X axis. It is a measure of the energy loss and is related to the viscous or loss modulus V by the factor of stress divided by strain:

$$V = (F_x/\pi R^2)/(y/h) = \text{Viscous Shear modulus}$$

The viscous modulus can be expressed as dynamic viscosity $\eta'$ by dividing the rotational frequency $\Omega$.

$$\eta' = V/\Omega = \text{Dynamic Shear Viscosity}$$

The origin and significance of the orthogonal stress components $F_x$, $F_y$ and the elastic and viscous properties can be visualized by considering a small segment $\Delta$ of the sample. In FIG. 2 the segment $\Delta$ is deformed. An elastic material will tend to return to its undeformed state. The force preventing that return is $F_y$. A viscous, inelastic material will display little tendency to return and hence a low $F_y$. As the discs rotate 90° the segment $\Delta$ will be returned to its undeformed state as is shown in FIG. 3. The force required to effect that return is $F_x$. An elastic material will require little or no force $F_x$ to return; its return being provided by its elasticity. A viscous material has little elastic tendency to return and will require a significant force $F_x$ to effect its return. Consequently, the elastic properties are reflected in $F_y$ and the viscous properties in $F_x$.

Because real materials are not everywhere linear, measurements are made at selected lateral displacements $y$ (strain amplitude) and at selected rotational speeds $\Omega$ (shear rate). Thereby, ranges of linearity can be identified.

FIG. 4 is a plot of elastic modulus E in dynes/cm$^2$, viscous modulus V in dynes/cm$^2$, and dynamic viscosity in poise ($\eta' = V/\Omega$) as a function of velocity or shear rate in sec$^{-1}$ for a polystyrene.

Viscoelastic data can also be plotted as a function of elapsed time to display the change in properties as polymerization or cure progresses. FIG. 5 displays E and V for three different epoxy/glass molding compounds A, B and C as they cured in an environment chamber during the test period.

FIG. 6 compares E and V for two ethylene propylene diene terpolymer elastomers A and B which show similar viscous properties, but different elastic properties; a difference which would not be revealed by their Mooney numbers even though they process differently.

The apparatus schematically shown in FIG. 1 derives the data representative of $F_x$ and $F_y$ from a force transducer 50 having orthogonal strain sensors of the strain gage or piezo-resistive types which provide a resistance proportional to the magnitude of the induced stress force component. Since the force components being measured are extremely small and the sensors extremely sensitive, any small force due to misalignment of the apparatus or any imbalance of the electrical bridge circuit in which the sensors are connected will produce an erroneous signal for $F_x$ or $F_y$ or both. For example, the sample is displaced in the Y direction by a linear actuator 46. If the sensors for providing a signal representative of $F_y$ are not precisely aligned with the Y axis, an inaccurate reading will result. Similarly, any misalignment of shafts 22, 28 will affect the accuracy of the signals representative of $F_y$ or $F_x$ or both.

According to the invention, errors are cancelled out by carrying out the measurements at y displacements and subtracting algebraically the results. In operation, the linear actuator laterally moves the stage 42 a preselected distance y for a preselected strain. At suitable intervals the sensors for providing signals representative of $F_x$ and $F_y$ are each sampled four times and the averages of the values of the signals are accumulated in storage. The stage is then moved to a different lateral displacement y. A second group of four more samplings of the sensor signals representative of $F_x$ and $F_y$ are made. The average of the first four $F_x$ and $F_y$ signal samples are subtracted from the average of the second four $F_x$ and $F_y$ samples, respectively. Any residual error is thereby cancelled. To illustrate, let us suppose that due to misalignment or electrical imbalance there is an error of e in the $F_x$ signal. Measurements of $F_x$ at $y_1$, will be $F_{x1} + e$. Measurements at $y_2$ will be $F_{x2} + e$. The difference will be $F_{x2} - F_{x1}$. The e cancels. Residual errors in $F_y$ are also cancelled. Therefore, an error vector at any angle will be resolved into its x and y direction signal components and be cancelled out.

Referring now to FIGS. 7 and 8, apparatus is shown which represents a complete embodiment of the generalized schematic apparatus of FIG. 1 and which incorporates the present invention. The mechanical aspects of the apparatus are housed within a body casting 100. The servo-motor 110 for driving the discs is carried within a housing portion 112 in a vertically reciprocable sleeve 114 reciprocated manually by a lever arm shaft 115 via a rack 116 and pinion 117 in a manner similar to the manual vertical feed of a drill press to lower the upper rotating member 124 on to the sample. A weight 118 provides a downward force when the sleeve is lowered and overbalances to hold the sleeve raised. A clamp lock 113 permits locking the spindle against vertical movement. A spring 111 counterbalances the weight of the sleeve and servo-motor.

A micrometer adjustable stop 119 provides a precision adjustment for sample thickness. A tachometer generator built into the servo-motor 110 provides a signal representative of angular velocity and is used in a conventional servo-positional feedback manner to accurately regulate motor speed.

The upper rotating member 124 driven by servo-motor 110 is in the form of a cylinder. The lower end face corresponds to the upper disc 24 described in connection with FIGS. 1-3. The lower rotating member 126 is in the form of a hollow cylinder with an upper end face which corresponds to lower disc 26 in FIGS. 1-3. Lower rotating member 126 is freely rotatable about shaft 128 by use of low friction bearings.

Shaft 128 is mounted on plate 142 which constitutes the movable or translatable portion of a micrometer stage 140, the lower plate 144 of which is fixed to the housing casting 100. A micrometer linear actuator 146 precisely positions the movable plate 142 and, thereby, the axis of the lower rotating member 126 with respect to the axis of the upper rotating member 124. Plate 142 moves to the left or right of FIG. 8 along the Y axis. The micrometer 146 extends and retracts through rotation by reversible servo-motor 148. A servo-potentiometer 149 provides a servo signal representative of the number of motor revolutions for conventional servo-positional feedback purposes.

The force components in the x and y directions are measured in transducer unit 150 by measuring the deflection of lower shaft 128. The lower extremity 129 of shaft 128 is square in cross-section to provide flat surfaces to each of which a pair of conventional high sensitivity piezo-resistive silicon strain gage devices (too small to be illustrated) is affixed to provide a resistance related to the elongation of each surface as shaft 128 is deflected. Such strain measuring devices are connected in conventional electrical bridge circuits and are calibrated to yield signals representative of force data for $F_x$ and $F_y$. One or more magnets 125 rotatable with the upper member 124 serve to actuate a reed switch device 127 fixed to the housing to provide samplings of the strain gage signals as the upper member rotates.

An environment chamber 170 encompasses the upper and lower rotating member 124, 126 and sample 130 under test. The environment chamber provides a desired temperature environment for the sample and is used to melt and temperature condition polymer samples or to effect a cure of the polymer under test. The chamber comprises an electrical resistance heated air convection oven. Resistance heaters 172 heat the air circulated about the sample 130 by a blower 174. Temperature sensors (not shown) are employed with a temperature programer and display to closely control the temperature of the sample. The environment chamber 170 is enclosed within a shroud 180 provided with a second blower 184 which draws ambient air to keep the exterior of the environment chamber cool and to cool and temperature stablize the portions of the upper and lower rotating members 124, 126 which emerge from the environment chamber. The front portion of the environment chamber 170 is hinged to allow access to the sample.

The data processor is a conventional microprocessor or computer which has been programed to store and additively accumulate data derived from the lateral and orthogonal strain sensor signals representative of $F_x$ and $F_y$ and is further provided with the function to arithmetically average them by dividing the sum by the number of signal samples added together. Since the signal samples are made at two different lateral displacements, errors of imbalance mechanical or electrical are cancelled out. The averaged data representative of $F_x$ and $F_y$ are put into a function generator or algebraic program which solves the equations for viscous and elastic moduli as above set out. These functions include as terms $F_x$ and $F_y$, the displacement y, and the radius of the disc squared. The displacement term is provided by a signal having a value representative of the strain selected. The radius squared term is a constant.

FIG. 9 shows the control panel which incorporates input controls for a data processor, output display and printout, and a temperature programer for the environment chamber.

At the upper right are two rows of five buttons for control of the speed of rotation of the upper rotating member 124. The angular velocity in radians per second is selected by pressing a multiplier button on the top row and a numerical button on the lower row. For example, 63 radians/second is selected by pressing the 10 multiplier button and the 6.3 radians/second button. Rotation is stopped by pressing the brake button.

The displacement $y$ of stage 142 is selected by pressing the desired strain button located at the right center of the panel. The displacement $y$ is expressed in terms of percent strain which is the displacement divided by the sample thickness. For a sample thickness of 0.100 inch a displacement $y$ of 0.005 inch is a 5% strain.

The upper central portion of the panel contains a digital display or readout of the calculated values of V and E. V is related to the measured $F_x$ divided by the strain and the sample area and E is related to the measured $F_y$ divided by the strain and the sample area. The result is displayed in dynes/cm$^2$ and is identified as V or E by lighting of the appropriate indicator light below the display.

The span and balance potentiometers are for calibration purposes.

The buttons at the upper left of the panel are for power on and off, environment chamber on and off and selection of the data processor program mode which will be described in connection with the operational description below. Start and end buttons allow the operator to begin and terminate the microprocessor program sequences.

The lower left of the panel incorporates a temperature programer which brings the sample in the environment chamber to a selected temperature or subjects the sample to a selected time-temperature profile or sequence useful in observing material properties during curing. The temperature in degrees Kelvin is digitally displayed.

A data printout device is located at the lower right of the panel. A code number for identification of the sample, the time, the speed, the strain, the temperature, and the calculated V and E results and printed for each test run.

Operation of the apparatus of FIGS. 7–9 will now be described. A polymer sample to be tested is placed upon the preheated lower rotating member 126 and the upper member 124 lowered by moving the lever shaft 115. The environment chamber 170 is closed about the sample and the sample is brought to testing temperature. If the polymer is in the form of solid pellets, a temporary cup is fashioned from thin metal about the upper end of member 126. Weight 118 presses the upper member 124 down on the pellets as they melt. When the melting has been completed further movement of the upper member is arrested by micrometer stop 119 set to provide a preselected sample thickness of say 0.100 inch. Excess polymer and the temporary cup are removed. When the sample reaches the preset desired temperature, the operator selects the microprocessor mode by pressing the desired mode button on the left of the control panel and the test sequence is initiated by the start button.

When normal mode is selected, the test will be executed at the temperature, angular velocity and strain preselected. Servo-motor 110 will rotate the upper member 124 at the selected angular velocity. Servo-motor 148 will run to extend micrometer linear actuator 146 to achieve a first displacement of the stage 142 of a $y_1$ determined by the percent strain selected. Four discrete samplings of the sensor signals representative of $F_x$ and $F_y$ are automatically made and the data are summed and stored in the data processor. Servo-motor 148 is automatically run to move micrometer linear actuator 146 to achieve a second displacement $y_2$ and four more discrete samplings of the sensor signals representative of $F_x$ and $F_y$ are made. The mathematical program function of the data processor averages the first four data measurements for each of $F_x$ and $F_y$ and subtracts the average of the second four data measurements of $F_x$ and $F_y$, respectively.

The difference is multiplied by the thickness of the sample and divided by the sample area and by the difference between the two displacements $y_1$ and $y_2$ to yield the calculated V and E, which results are displayed on the digital readout and may be printed if desired by the printer along with the identification code, strain, speed, temperature and time. The data processor is programed to cause the servo-motor 148 to return the stage 142 to a displacement of zero. The data processor checks the mode selected by the operator and ends the run when the test is over.

The frequency mode, when selected by the operator, steps down through a spectrum of angular velocities from that selected by the operator and performs the V and E calculations as above described for each angular velocity. If the operator selects frequency mode and a maximum angular velocity of 10 radians/second, eight $F_x$ and eight $F_y$ measurements are made and averaged at each of 10, 6.3, 4.0, 2.5, 1.6, 1.0, 0.63, 0.40, 0.25 and 0.16 radians/second. The microprocessor then terminates the test run. As each sequence of measurements is completed the calculated V and E results are displayed and, if desired printed by the printer.

Normal mode plus temperature mode is selected when the temperature is to be increased as the test progresses. The low and high temperatures, and incremental increase in temperature between tests are selected on the temperature programer by the operator. The temperature programer is switched from local to remote. After a test sequence at each temperature, the system will increase the temperature by the selected increment, dwell about three minutes for stabilization and run the test at the new temperature.

Selection of frequency mode plus temperature mode will cause the system to perform a sequence of tests at decreasing speeds as described for the frequency mode at each incremental temperature.

Cure mode differs from normal mode in that the test is repeated at intervals automatically. It is useful for observing changes in rheological properties as a polymer progresses toward a cure. The environment chamber provides the desired cure temperature or cure temperature profile.

Calibrate mode is used during calibration of the system.

Although the principal use of the invention is in the measurement of rheological properties of polymeric materials, the invention is useful for categorization or discernment of deviations from norms for a wide variety of materials including foodstuffs, petrochemicals, explosives, biological liquids such as blood, and other liquids, pastes, suspensions, slurries, emulsions, etc.

I claim:

1. A method for automatically determining a rheological property of a material with an eccentric rotating disc rheological test apparatus comprising, in order, the steps of placing a sample of the material between and in contact with the confronting circular faces of a pair of rotatable members, rotatively driving one of the members, laterally displacing the axis of rotation of one of the members with respect to the other a first predetermined distance to impart a strain to the material, producing a first signal having a value representative of the stress in one of the rotating members, laterally displacing the axes a second predetermined distance, producing a second signal having a value representative of the stress in the rotating member, and producing a third signal having a value of the difference between the first and second signals divided by the difference between the first and second predetermined distances, said third signal being representative of the rheological property.

2. The method of claim 1 wherein the rheological property is the elastic modulus and the first and second signals have values representative of the stress in the rotating member in the direction of lateral displacement of the axes.

3. The method of claim 1 wherein the rheological property is the viscous modulus and the first and second signals have values representative of the stress in the rotating member in the direction orthogonal to the direction of lateral displacement.

4. A method for automatically determining the elastic and viscous moduli of a material with an eccentric rotating disc rheological test apparatus comprising the steps of placing a sample of the material between and in contact with the confronting circular faces of a pair of rotatable members, rotatively drivng one of the members, laterally displacing the axis of rotation of one of the members with respect to the other a first predetermined distance to impart a strain to the material, producing a first pair of signals having values representative of the stress in one of the rotating members in the direction of lateral displacement and in the orthogonal direction, laterally displacing the axes a second predetermined distance, producing a second pair of signals having values representative of the stress in the rotating member in the lateral and orthogonal directions, producing a signal having a value representative of the elastic modulus, which signal is a function of the difference of the values of the signals of the first and second pair representative of stress in the direction of lateral displacement and a signal having a value representative of the difference between the first and second predetermined distances, and producing a signal having a value representative of the viscous modulus, which signal is a function of the difference of the values of the signals of the first and second pair representative of the stress in the direction orthogonal to the direction of lateral displacement and a signal having a value representative of the difference between the first and second predetermined distances.

* * * * *